United States Patent
Meyer et al.

(10) Patent No.: US 10,745,736 B2
(45) Date of Patent: Aug. 18, 2020

(54) MARKERS FOR MOOD DISORDERS

(71) Applicant: Centre for Addiction and Mental Health, Toronto (CA)

(72) Inventors: Jeffrey Meyer, Toronto (CA); Ken Evans, Toronto (CA); Jian Chen, Toronto (CA); Suzanne Ackloo, Toronto (CA); Moyez Dharsee, Toronto (CA)

(73) Assignee: CENTRE FOR ADDICTION AND MENTAL HEALTH, Toronto (CA)

( * ) Notice: Subject to any disclaimer, the term of this patent is extended or adjusted under 35 U.S.C. 154(b) by 0 days.

(21) Appl. No.: 15/514,956

(22) PCT Filed: Oct. 1, 2015

(86) PCT No.: PCT/CA2015/050990
§ 371 (c)(1),
(2) Date: Mar. 28, 2017

(87) PCT Pub. No.: WO2016/049770
PCT Pub. Date: Apr. 7, 2016

(65) Prior Publication Data
US 2017/0226559 A1 Aug. 10, 2017

Related U.S. Application Data

(60) Provisional application No. 62/058,286, filed on Oct. 1, 2014.

(51) Int. Cl.
| | | |
|---|---|---|
| *C12Q 1/68* | (2018.01) | |
| *G01N 33/567* | (2006.01) | |
| *C12Q 1/26* | (2006.01) | |
| *C40B 40/10* | (2006.01) | |
| *C12N 9/06* | (2006.01) | |
| *C07K 7/08* | (2006.01) | |
| *C07K 7/06* | (2006.01) | |
| *A61B 5/11* | (2006.01) | |
| *A61B 5/145* | (2006.01) | |
| *G01N 33/50* | (2006.01) | |

(52) U.S. Cl.
CPC ............ *C12Q 1/26* (2013.01); *A61B 5/1127* (2013.01); *A61B 5/145* (2013.01); *C07K 7/06* (2013.01); *C07K 7/08* (2013.01); *C12N 9/0022* (2013.01); *C12Q 1/68* (2013.01); *C12Y 104/03004* (2013.01); *C40B 40/10* (2013.01); *G01N 33/5008* (2013.01); *G01N 2333/90638* (2013.01); *G01N 2560/00* (2013.01); *G01N 2800/304* (2013.01)

(58) Field of Classification Search
None
See application file for complete search history.

(56) References Cited

FOREIGN PATENT DOCUMENTS

WO WO 2008/021290 A2 2/2008

OTHER PUBLICATIONS

International Preliminary Report on Patentability for PCT/CA2015/050990, dated Apr. 4, 2017.
International Search Report and Written Opinion for PCT/CA2015/050990, dated Jan. 7, 2016.
Domenici et al., Plasma protein biomarkers for depression and schizophrenia by multi analyte profiling of case-control collections. PLoS One. Feb. 11, 2010;5(2):e9166. doi: 10.1371/journal.pone.0009166.
Meyer et al., Elevated monoamine oxidase a levels in the brain: an explanation for the monoamine imbalance of major depression. Arch Gen Psychiatry. Nov. 2006;63(11):1209-16.
Peehl et al., The significance of monoamine oxidase-A expression in high grade prostate cancer. J Urol. Nov. 2008;180(5):2206-11. doi: 10.1016/j.juro.2008.07.019. Epub Sep. 20, 2008.
Pintar et al., Monoamine oxidase (MAO) activity as a determinant in human neurophysiology. Behav Genet. Feb. 1982;12(1):53-68.
Sivasubramaniam et al., A comparative study of the expression of monoamine oxidase-A and -B mRNA and protein in non-CNS human tissues. Cell Tissue Res. Sep. 2003;313(3):291-300. Epub Jul. 26, 2003.
Strausberg et al., Monoamine oxidase A [*Homo sapiens*]. GenBank Accession No. AAH08064.1. Jul. 15, 2006. www.ncbi.nlm.nih.gov/protein/AAH08064.

*Primary Examiner* — Olga N Chernyshev
(74) *Attorney, Agent, or Firm* — Wolf, Greenfield & Sacks, P.C.

(57) ABSTRACT

Disclosed is a method for diagnosing a mood disorder or susceptibility to a mood disorder, including depressive disorders and bipolar disorder, from a biological sample taken from a subject. The method includes detecting markers of monoamine oxidase-A (MAO-A) in the biological sample; determining MAO-A concentration from the markers; and correlating the MAO-A concentration in the biological sample to a control group which does not have a mood disorder in order to diagnose or determine susceptibility to the mood disorder in the subject. Also disclosed is a method of detecting peripheral markers of MAO-A for the diagnosis of a mood disorder or susceptibility to a mood disorder. Also provided are polypeptide markers.

5 Claims, 9 Drawing Sheets
Specification includes a Sequence Listing.

FIGURE 1

Ctrl-sample 1-P21397-Amine oxidase Alt Name: AAREVLNGLGK.2y7 (Unknown) 564.3/700.4 –
Meyer_controlS1_1.wiff (sampl..) Area:3.882e5 – Height 6.276e3

Ctrl-sample 2-P21397-Amine oxidase Alt Name: AAREVLNGLGK.2y7 (Unknown) 564.3/700.4 –
Meyer_controlS2_1.wiff (sample 1) Area:3.733e5 – Height 6.042e3 dep-sample 3-P21397-Amine oxidase Alt Name: AAREVLNGLGK.2y7 (Unknown) 564.3/700.4 –
Meyer_depressionS3_1b.wiff (sampl..) Area:7.893e5 – Height 1.204e3 dep-sample 4-P21397-Amine oxidase Alt Name: AAREVLNGLGK.2y7 (Unknown) 564.3/700.4 –
Meyer_depressionS4_1.wiff (sample) Area:5.616e5 – Height 8.751e3 dep-sample 5-P21397-Amine oxidase Alt Name: AAREVLNGLGK.2y7 (Unknown) 564.3/700.4 –
Meyer_depressionS5_1.wiff (sample) Area:7.463e5 – Height 1.072e3

SEQUENCE LISTING

```
<160> NUMBER OF SEQ ID NOS: 7

<210> SEQ ID NO 1
<211> LENGTH: 20
<212> TYPE: PRT
<213> ORGANISM: homo sapiens

<400> SEQUENCE: 1

Asn Glu His Val Asp Tyr Val Asp Val Gly Gly Ala Tyr Val Gly Pro
1               5                   10                  15

Thr Gln Asn Arg
            20

<210> SEQ ID NO 2
<211> LENGTH: 6
<212> TYPE: PRT
<213> ORGANISM: homo sapiens

<400> SEQUENCE: 2

Ile Leu Arg Leu Ser Lys
1               5

<210> SEQ ID NO 3
<211> LENGTH: 10
<212> TYPE: PRT
<213> ORGANISM: homo sapiens

<400> SEQUENCE: 3

Phe Ser Val Thr Asn Gly Gly Gln Glu Arg
1               5                   10

<210> SEQ ID NO 4
<211> LENGTH: 13
<212> TYPE: PRT
<213> ORGANISM: homo sapiens

<400> SEQUENCE: 4

Tyr Val Ile Asn Ala Ile Pro Pro Thr Leu Thr Ala Lys
1               5                   10

<210> SEQ ID NO 5
<211> LENGTH: 11
<212> TYPE: PRT
<213> ORGANISM: homo sapiens

<400> SEQUENCE: 5

Ala Ala Arg Glu Val Leu Asn Gly Leu Gly Lys
1               5                   10

<210> SEQ ID NO 6
<211> LENGTH: 14
<212> TYPE: PRT
<213> ORGANISM: homo sapiens

<400> SEQUENCE: 6
```

```
Asp Val Pro Ala Val Glu Ile Thr His Thr Phe Trp Glu Arg
1               5                   10

<210> SEQ ID NO 7
<211> LENGTH: 11
<212> TYPE: PRT
<213> ORGANISM: homo sapiens

<400> SEQUENCE: 7

Phe Val Gly Gly Ser Gly Gln Val Ser Glu Arg
1               5                   10
```

MARKERS FOR MOOD DISORDERS

RELATED APPLICATIONS

This application is a national stage filing under 35 U.S.C. § 371 of international PCT application, PCT/CA2015/050990, filed Oct. 1, 2015, which claims priority under 35 U.S.C. § 119(e) to U.S. Provisional Application, U.S. Ser. No. 62/058,286, filed on Oct. 1, 2014, each of which is incorporated herein by reference.

FIELD OF THE INVENTION

The present invention relates to the diagnosis and treatment of mood disorders and markers therefor.

BACKGROUND OF THE INVENTION

Mood disorders, such as depressive disorders and bipolar disorder, are serious health burdens affecting approximately 10% of the population. Bipolar disorder is estimated to affect 1.6% of the population, whereas major depressive disorder (MDD) is estimated to have a lifetime prevalence in the general population of between 10% and 25% for women and from 5% to 12% for men. The World Health Organization predicts the MDD will be the second greatest contributor to the global burden of disease by 2020.

Although the symptoms of MDD are frequently experienced by most individuals, clinical depression is different in that feelings of unhappiness and disappointment become quantitatively different, pervasive or interfere with normal function (Doris A et al., 1999, Lancet 354:1369-1375). The Diagnostic and Statistic Manual, version IV (DSM-IV) describes an individual as having major depressive episode when five or more of the following symptoms are present nearly everyday for a two week period: 1) depressed mood most of the day; 2) markedly diminished interest or pleasure in all, or almost all, activities most of the day; 3) significant weight loss when not dieting or weight gain, or decrease or increase in appetite; 4) insomnia or hypersomnia; 5) psychomotor agitation or retardation; 6) fatigue or loss of energy; 7) feelings of worthlessness or excessive or inappropriate guilt; 8) diminished ability to think or concentrate or indecisiveness; and 9) recurrent thoughts of death (DSM-IV, 1994).

The hypothesis that mood disorders have a biological component has been studied since the 1960's. The catecholamine and indoleamine hypotheses of mood disorders were first proposed in the mid-1960's in two separate reviews (Coppen A, 1967, Br J Psychiatry 113: 1237-1264; Schildkraut J J, Am. J. Psychiatry 122:509-522). The catecholamine theory of mood disorders proposed that depression resulted from decreased norepinephrine and mania was the result of elevated norepinephrine levels at central adrenergic receptor sites (Schildkraut J J, supra). The indoleamine hypothesis was derived from evidence suggesting that serotonin (5-HT) was responsible for the disorders, specifically, decreased 5-HT levels caused depression (Coppen, supra).

Interest in norepinephrine and 5-HT as important neurotransmitters in mental illness arose when subjects given the tranquilizing substance reserpine, known to deplete brain amine levels, displayed profound behavioural depression during the course of treatment (Coppen, supra; Peterfy G et al., 1976, Psychoneuroendocrinology I:243-253; Quetsch R M et al., 1959, Circulation 19: 366-375). A study by Lingjaerde (1963, Acta Psychiatr Scand 39(Suppl 170): 1-109) reported similar findings when subjects were administered tetrabenazine, a compound with similar amine depleting effects. Clinical studies measuring peripheral levels of 5-HT and norepinephrine metabolites, 5-HIAA and MHPG respectively, have been conducted in an attempt to support the catecholamine and indoleamine hypotheses. Peripheral measures in psychiatric illnesses are the preferred way to obtain information on mood state-dependent changes associated with the disorders. However, results from several studies suggest that peripheral measures of 5-HT and norepinephrine metabolism from plasma, urine and cerebrospinal fluid (CSF) are inconsistent and fail to provide any evidence to support the catecholamine and indoleamine hypotheses (Geracioti Jr T D et al., 1997, Depress Anxiety 6:89-94; Placidi G P et al., 2001, Biol Psychiatry 50: 783-791 and references therein).

Strong evidence to support the catecholamine and indoleamine hypotheses has come from studies examining the mechanism of action of antidepressants. Most antidepressants have been developed to target one or more of the elements involved in the reuptake, synthesis and/or catabolism of norepinephrine or 5-HT. The result of chronic treatment with any of these drugs is increased synaptic concentrations of 5-HT or norepinephrine, suggesting that the pathophysiology of MDD involves decreased CNS levels of these neurotransmitters. However, the primary synthetic or catabolic component responsible for the increase in synaptic concentrations of 5-HT or norepinephrine remains elusive.

Monoamine oxidase-A (MAO-A) is an enzyme that metabolizes 5-HT, norepinephrine and dopamine in the brain. It is the main route for metabolism of 5-HT, and an important route of metabolism for the other two monoamines. All three of these monoamines are high affinity substrates for MAO-A (Fowler C et al., Substrate-Selective Interaction Between Monoamine Oxidase and Oxygen. In: Singer T, Von Korff R, Murphy D, eds. *Monoamine Oxidase: Structure, Function and Altered Functions*. New York: Academic Press, Inc.; 1979:145-151; Kinemuchi H et al., Substrate Specificities of the Two Forms of Monoamine Oxidase. In: Tipton K, Dostert P, Strolin-Benedetti M, eds. *Monoamine Oxidase and Disease: Prospects for Therapy with Reversible Inhibitors*. New York: Academic Press, Inc.; 1984:53-62; Schoepp D D et al., 1981, J Neurochem 36(6): 2025-2031; White H et al., Characterization of Multiple Substrate Binding Sites of MAO. In: Singer T, Von Korff R, Murphy D, eds. *Monoamine Oxidase: Structure, Function and Altered Functions*. New York: Academic Press, Inc.; 1979:145-151; Houslay M D et al., 1974, Biochem J 139 (3):645-652). MAO-A has been detected in cells that release these monoamines, with the highest levels in norepinephrine releasing neurons (Konradi C et al., 1988, Neuroscience 26(3):791-802; Luque J M et al., 1995, J Comp Neurol 363(4):665-680; Saura J et al., 1996, Neuroscience 70(3): 755-774; Konradi C et al., 1989, Neuroscience 33(2):383-400; and Moll G et al., 1990, J Neural Transm Suppl 32:67-77) (MAO-A in cells that release monoamines and MAO-A in cells that do not release monoamines are both believed to contribute to monoamine metabolism (Youdim M B et al., 2006, Nat Rev Neurosci 7(4):295-309)). Medications that inhibit MAO-A, and MAO-A knockout models are associated with greater levels of extracellular 5-HT in prefrontal cortex, hippocampus, and superior raphe nuclei, norepinephrine in prefrontal cortex and hippocampus, and dopamine in striatum. In brain, the predominant location for this enzyme is on the outer mitochondrial membranes in neurons (Saura J et al., supra). Monoamine oxidase-A density is highest in locus coeruleus, moderate in the cortex, hippocampus, and striatum, low in cerebellar cortex and minimal in white matter (S aura J et al., supra; and S aura et al., 1992, J Neurosci 12(5):1977-1999). Brain MAO-A density is highly correlated with MAO-A activity (Saura et al., ibid).

Previous studies have shown brain MAO-A levels are elevated in patients with MDD. For example, a recent study measured an index of MAO-A density in 17 major depressive episode (MDE) subjects (secondary to MDD) and 17 healthy subjects with [$^{11}$C] harmine PET. The subjects were otherwise healthy. Depressed subjects were drug free for at least five months although most were antidepressants naïve. Depressed subjects were aged 18-50, met DSM-IV diagnosis of current MDE and MDD verified by SCID for DSM-IV, and a psychiatric consultation, non-smoking and had greater than 17 on the 17 item HDRS. The index of MAO-A binding was highly significantly elevated ($p<0.001$) in each region, with an average magnitude 34 percent (or two standard deviations) in the depressed subjects (Meyer et al., 2006, Arch Gen Psychiatry 63(11):1209-1216). The study by Meyer et al., shows that brain MAO-A is elevated in early onset depression (prior to age 40) because the magnitude was large, the sample was carefully defined, the method was selective for brain MAO-A and there has never previously been a post mortem study of brain MAO-A levels in medication free depressed subjects (Meyer et al., 2008, Semin Nucl Med 38(4):287-304). Previous post mortem studies of MAO-A did not examine the question as to whether MAO-A is elevated in medication free, early onset depression. The most reasons are lack of specificity for MAO-A, diagnostic non-specificity by sampling of suicide victims rather than depressed suicide victims, inclusion of subjects who recently took medication, and/or overdosed, no differentiation between early onset depression and late onset depression, and small sample size. The results seen with MAO-A levels in brain have been replicated by Meyer et al., (2009, Arch Gen Psych 66:1304-12). In addition, Johnson et al., (2011, Neuropsychopharmacology 36:2139-48) reported greater MAO-A density during MDE applying immunoblotting techniques in post-mortem prefrontal cortex.

Since imaging the brain during a MDE is technically challenging and slightly impractical in the clinical setting, a peripheral measure correlating the increase in MAO-A levels in the brain to MDD is desired. However, peripheral and central measures, such as the brain, do not always correlate. For example, platelet 5-HT$_{2A}$ receptor density does not correlate with regional brain 5-HT$_{2A}$ density (Cho R et al., 1999, Neurosci Lett 261(3):139-142). Moreover, as mentioned above, inconsistent results have been obtained when monoamine metabolite levels are measured in blood in an effort to correlate with disease state. These results seem at odds to the behavioural patterns of subjects depleted of certain brain monoamines. The ability to measure the increase in MAO-A levels seen in the brain, using blood, for example, is desired.

SUMMARY OF THE INVENTION

According to an aspect of the present invention, there is provided a method for diagnosing a mood disorder or susceptibility to a mood disorder from a biological sample taken from a subject. The method comprising the steps of: detecting one or more markers of monoamine oxidase-A (MAO-A) in the biological sample; determining MAO-A concentration from the one or more markers; and correlating the MAO-A concentration in the biological sample to a control group which does not have a mood disorder in order to diagnose the mood disorder in the subject.

According to another aspect of the present invention, there is provided a method of detecting peripheral markers of monoamine oxidase-A (MAO-A) for the diagnosis of a mood disorder or susceptibility to a mood disorder. The method comprising the steps of: obtaining a biological sample from a subject symptomatic with the mood disorder or asymptomatic for the mood disorder and has previously been symptomatic for the mood disorder; subjecting the biological sample to a process for obtaining an enriched protein mixture that contains the MAO-A protein, converting the MAO-A protein containing protein mixture into peptides using a protease, and analyzing the resulting peptide sample using selected reaction monitoring mass spectrometry (MS); identifying transitions in the MAO-A polypeptides from the MS; and comparing the transitions to a control group which does not have a mood disorder in order to identify a peripheral marker of MAO-A.

According to a further aspect of the present invention, there is provided a method of diagnosing a mood disorder or susceptibility to a mood disorder from a biological sample taken from a subject. The method comprising the steps of: detecting markers of monoamine oxidase-A (MAO-A) in the biological sample, wherein the markers are selected from a group of polypeptides derived from protease-induced hydrolysis of the MAO-A protein, comprising one or more polypeptides including, but not limited to, the amino acid sequences: NEHVDYVDVGGAYVGPTQNR (SEQ ID NO:1); ILRLSK (SEQ ID NO:2); FSVTNGGQER (SEQ ID NO:3); YVINAIPPTLTAK (SEQ ID NO:4); AAREVLNGLGK (SEQ ID NO:5); DVPAVEITHTFWER (SEQ ID NO:6); and FVGGSGQVSER (SEQ ID NO:7); determining MAO-A concentration from the markers; and correlating the MAO-A concentration in the biological sample to a control group which does not have a mood disorder in order to diagnose the mood disorder or susceptibility to a mood disorder in the subject.

In one embodiment, the biological sample is blood. Preferably, the biological sample is plasma.

In another embodiment, the method comprises processes for obtaining an enriched protein mixture containing MAO-A proteins or fragments, for example, but are not limited to depletion procedures to remove high abundant proteins in blood or plasma, for example, but not limited to immunoprecipitation against MAO-A protein, ion-exchange and/or reversed phase interaction-based chromatographic isolation, protein precipitation, protein enrichment using a molecular weight cut-off filter, and the like. For example, but not wishing to be considered limiting in any manner, the present invention also contemplates removal of the most abundant proteins from plasma, for example, the most abundant 15, 14, 13, 12, 11, 10, 9, 8, 7, 6, 5, 4, 3, or most abundant protein before analysis of a plasma sample. One example of such a protein is albumin.

In an embodiment, the biological sample may be subjected to one or more enzymatic procedures, for example, but not limited to protease treatment. For example, the protease may be a biological reagent that is capable of cleaving MAO-A into polypeptides at specific amino acid position, for example, but not limited to serine proteases, threonine proteases, cysteine proteases and aspartate proteases. These include, but are not limited to, trypsin, chemotrypsin and the like.

In a further embodiment the markers are selected from a group of polypeptides comprising or consisting of all the amino acid sequences derived from enzyme cleavage of MAO-A, including, but not limited to: NEHVDYVDVG-GAYVGPTQNR (SEQ ID NO:1); ILRLSK (SEQ ID NO:2); FSVTNGGQER (SEQ ID NO:3); YVINAIPPTLTAK (SEQ ID NO:4); AAREVLNGLGK (SEQ ID NO:5); DVPAVEITHTFWER (SEQ ID NO:6) and FVGGS-GQVSER (SEQ ID NO:7).

In still other aspects of the invention the subject may be symptomatic for the mood disorder or the subject may be asymptomatic for the mood disorder without previously having been symptomatic for the mood disorder. The subject may also be asymptomatic for the mood disorder and may previously have been symptomatic for the mood disorder, with an elevated level of the MAO-A indicating a greater risk of recurrence of symptoms.

According to an aspect of the present invention there is provided a polypeptide comprising the amino acid sequence NEHVDYVDVGGAYVGPTQNR (SEQ ID NO:1). In a further aspect, there is provided a polypeptide consisting of amino acid sequence NEHVDYVDVGGAYVGPTQNR (SEQ ID NO:1).

According to an aspect of the present invention there is provided a polypeptide comprising the amino acid sequence ILRLSK (SEQ ID NO:2). In a further aspect, there is provided a polypeptide consisting of amino acid sequence ILRLSK (SEQ ID NO:2).

According to an aspect of the present invention there is provided a polypeptide comprising the amino acid sequence FSVTNGGQER (SEQ ID NO:3). In a further aspect, there is provided a polypeptide consisting of amino acid sequence FSVTNGGQER (SEQ ID NO:3)

According to an aspect of the present invention there is provided a polypeptide comprising the amino acid sequence YVINAIPPTLTAK (SEQ ID NO:4). In a further aspect, there is provided a polypeptide consisting of the amino acid sequence YVINAIPPTLTAK (SEQ ID NO:4).

According to an aspect of the present invention there is provided a polypeptide comprising the amino acid sequence AAREVLNGLGK (SEQ ID NO:5). In a further embodiment, there is provided a polypeptide consisting of the amino acid sequence AAREVLNGLGK (SEQ ID NO:5).

According to an aspect of the present invention there is provided a polypeptide comprising the amino acid sequence DVPAVEITHTFWER (SEQ ID NO:6). According to a further aspect, there is provided a polypeptide consisting of the amino acid sequence DVPAVEITHTFWER (SEQ ID NO:6).

According to an aspect of the present invention there is provided a polypeptide comprising the amino acid sequence FVGGSGQVSER (SEQ ID NO:7). According to a further aspect, there is provided a polypeptide consisting of the amino acid sequence FVGGSGQVSER (SEQ ID NO:7).

In all of the above cases, the polypeptide does not comprise full length MAO-A as would be known in the art.

According to a further aspect, there is provided one or more amino acid or polypeptide sequences that are peripheral markers for brain MAO-A concentration. The amino acid or polypeptide sequences may comprise or consist of the sequence defined herein, for example, SEQ ID NOs: 1, 2, 3, 4, 5, 6, or 7. In alternate aspects, the present invention further contemplates that the amino acid or polypeptide sequences may be any length, for example 5, 6, 7, 8, 9, 10, 11, 12, 13, 14, 15, 16, 17, 18, 19, 20, 30, 40, 50, 60, 70, 80, 90, 100, 200 or more amino acids in length. Further, the markers may be defined by a range of any two of the values specifically recited herein or any values therein between.

In another embodiment the mood disorder is selected from major depressive disorder, dysthymia and depressive disorder not otherwise specified.

In a further embodiment the mood disorder is major depressive disorder or bipolar disorder.

In a further embodiment, there is provided an antibody or fragment thereof that binds to any polypeptide described herein, for example, to the polypeptide sequences defined by SEQ IDs 1, 2, 3, 4, 5, 6 or 7. Also provided are nucleic acid sequences encoding the antibody or a fragment thereof

BRIEF DESCRIPTION OF THE DRAWINGS

These and other features of the invention will become more apparent from the following description in which reference is made to the following drawings.

DESCRIPTION OF THE INVENTION

The following description is of a preferred embodiment by way of example only and without limitation to the combination of features necessary for carrying the invention into effect.

The present invention relates generally to diagnosis of psychiatric disorders and markers therefor. More specifically, the invention relates to diagnostic and prognostic markers for mood disorders. The present invention also relates to identifying subjects that have increased concentration of one or more MAO-A markers in serum compared to a control group, for example a control group that does not have depressive disorder.

Mood disorders as used herein include, but are not limited to, depressive disorders, such as major depressive disorder (MDD), dysthymia and depressive disorder not otherwise specified, and bipolar disorder (or manic-depression). MDD can be further subcategorized as being atypical depression, melancholic depression, psychotic major depression, catatonic depression, postpartum depression and seasonal affective disorder. Depressive disorders not otherwise specified include recurrent brief depression and minor depressive disorder. Bipolar disorder can also be subcategorized into bipolar I, bipolar II, cyclothymia and bipolar disorder not otherwise specified.

The present invention provides a method for diagnosing a mood disorder or susceptibility to a mood disorder from a biological sample taken from a subject. This method includes detecting one or more markers of monoamine oxidase-A (MAO-A) in the biological sample. The present invention also provides that the MAO-A concentration in the sample is determined from the one or more markers. Finally, the MAO-A concentration in the biological sample is correlated to a control group which does not have a mood disorder or susceptibility to a mood disorder in order to diagnose the mood disorder or susceptibility to the mood disorder in the subject.

Markers of MAO-A can include, but are not limited to, polypeptides corresponding to all or portions of the MAO-A protein. However, certain peptides are preferred as described herein. The markers or polypeptides identified herein may be employed in methods as described. Further, the markers or polypeptide may be useful in additional ways, for example in the generation of antibodies for immunological testing and assays and/or as controls in mass spectroscopy, immunological and other research methods and protocols.

In a preferred embodiment, these markers are identified/detected from a biological sample using mass spectrometry or immunological methods as are known in the art. In particular, Liquid Chromatography/Selected Reaction Monitoring-Mass Spectrometry (LC/SRM-MS) is used to quantify specific MAO-A peptide fragments (transitions) that can be used as markers to diagnose the mood disorder or susceptibility to a mood disorder. Transition peptides of the present invention include peptides shown in FIG. 1, namely NEHVDYVDVGGAYVGPTQNR (SEQ ID NO:1); ILRLSK (SEQ ID NO:2); FSVTNGGQER (SEQ ID NO:3); YVINAIPPTLTAK (SEQ ID NO:4); AAREVLNGLGK (SEQ ID NO:5); DVPAVEITHTFWER (SEQ ID NO:6) and FVGGSGQVSER (SEQ ID NO:7). Preferably, the transition peptides are selected from NEHVDYVDVGGAYVGPTQNR (SEQ ID NO:1); YVINAIPPTLTAK (SEQ ID NO:4); AAREVLNGLGK (SEQ ID NO:5); and FVGGSGQVSER (SEQ ID NO:7). Most preferred is AAREVLNGLGK (SEQ ID NO:5).

In a further embodiment, antibodies directed to these transition peptides can be developed to extract, detect and/or quantify differences in MAO-A levels in subjects being tested or suspected of having a mood disorder compared to a control group. At the protein level various techniques exist to identify changes in protein levels. These include, but are not limited to, immunoblotting, immunoprecipitation, and enzyme-linked immunosorbent assay (ELISA).

Comparisons of mass-spectometry spectra from suspected mood disorder subjects and controls, for example comparisons of peptide fragment sequence information can be carried out using spectra processed in MATLB with script called "Qcealign" (see for example WO2007/022248, herein incorporated by reference) and "Qpeaks" (Spectrum Square Associates, Ithaca, N.Y.), or CIPHERGEN PEAKS 2.1™ software. The processed spectra can then be aligned using alignment algorithms that align sample data to the control data using minimum entropy algorithm by taking baseline corrected data (see for example WIPO Publication WO2007/022248, herein incorporated by reference). The comparison result can be further processed by calculating ratios. Protein expression profiles can be discerned.

The present invention also provides a method for detecting peripheral markers of MAO-A for the diagnosis of a mood disorder or for determining susceptibility to mood disorder. The method includes obtaining a biological sample from a subject symptomatic with the mood disorder or asymptomatic for the mood disorder and has been symptomatic for the mood disorder. The present invention also provides subjecting the biological sample to SRM-MS or one or more immunological methods. With respect to mass spectroscopy, the transitions in MAO-A are identified from the MS. Finally, the transitions are correlated to a control group that does not have a mood disorder in order to identify a peripheral marker of MAO-A.

A raw SRM-MS dataset may be obtained from a biological sample from a subject symptomatic with a mood disorder or asymptomatic for the mood disorder, but who has previously been symptomatic for the mood disorder. The dataset is processed to identify transition peaks and determine peak area. An example of suitable software to process the dataset is MultiQuant software. A t smoothing window can be set prior to peak area integration. Significance analysis can be conducted using statistical analysis software, such as R and SPSS.

For each transition (feature) measured in a given biological sample in replicate SRM-MS experiments, numerical measures such as mean peak area and peak area coefficient of variation (CV) are calculated. Using each feature, within-group mean peak area and CV can be calculated for the mood disorder and control groups from the individual sample mean peak area values.

Fold-change can be derived for each feature from the ratio of mean peak area in the mood disorder samples to mean peak area in control samples. Positive fold-changes represent increased expression in the mood disorder group.

Without wishing to be limiting or bound by theory in any manner, those peptides for which at least two transition features displayed a fold-change of 1.20 or greater and a within-group CV of 0.20 or less would be suitable candidates for use as markers for the diagnosis of the mood disorder.

The results provided herein show that one or more MAO-A markers are elevated in the plasma of patients with mood disorder. The results also suggest that the levels of peripheral polypeptide sequences described herein correlate with depression and provide an index of MAO-A levels in the brain. Thus the present invention also contemplates determining if a subject exhibits one or more MAO-A markers and if the level of the one or more MAO-A markers is elevated compared to a control group, for example, a control group that does not have mood disorder, in order to determine which subjects should be subjected to continued screening and/or monitoring, counseling, additional psychological testing, one or more genetic or other tests that predict, determine or diagnose mood disorder(s) or susceptibility thereto, and/or family screening. The present application also contemplates treating a patient with elevated MAO-A levels using therapies known in the art in order to improve mood, and/or prevent or reduce susceptibility to a mood disorder or the symptoms associated therewith.

The present invention also contemplates one or more antibodies that are capable of binding to any one of the amino acid or polypeptide sequences described herein. In a preferred embodiment, the antibody is a monoclonal antibody. Also contemplated are nucleotide sequences comprising the one or more antibodies describe herein.

Antibodies, including monoclonal antibodies can be prepared using a wide variety of techniques known in the art including, for example, hybridoma, recombinant, and phage display technologies, or a combination thereof. For example, monoclonal antibodies can be produced using hybridoma techniques including those known in the art, for example, but not wishing to be considered limiting in any manner, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" refers to an antibody that is derived from a single clone, including any eukaryotic, prokaryotic, or phage clone, and is not meant to be limited by the method by which it is produced.

Methods for producing and screening for specific antibodies using hybridoma technology are routine and also well known in the art. As an example, but not to be considered limiting in any manner, an animal capable of eliciting an immune response to an antigen (for example, mice) can be immunized with an antigen, for example a polypeptide as described herein, a fragment or variant thereof, a fusion protein, or a cell expressing an antigen, polypeptide or fragment or variant thereof. Once an immune response is detected, e.g., antibodies specific for the antigen are detected in the mouse serum, the mouse spleen is harvested and splenocytes isolated. The splenocytes are then fused by well known techniques to any suitable cells, for example, myeloma cells or the like. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating polyclonal and monoclonal antibodies as well as antibodies produced by the method comprising culturing a hybridoma cell secreting an antibody wherein, preferably, the hybridoma is generated by fusing splenocytes isolated from a mouse or other animal immunized with a polypeptide of the invention with myeloma cells and then screening the hybridomas resulting from the fusion for hybridoma clones that secrete an antibody able to bind a polypeptide of the invention.

Other well known methods for producing antibodies also may be employed. Such methods include but are not limited to Epstein Barr Virus (EBV) transformation protocols, for example, in Current Protocols in Immunology, Coligan et al., Eds., 1994, John Wiley & Sons, NY, which is hereby incorporated in its entirety by reference.

The present invention also contemplates the production of antibody fragments which recognize the polypeptides as described herein, fragments thereof or specific epitopes therein. Such antibody fragments may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

Antibodies that bind to an antigen can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make antibodies that bind to an antigen include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988), herein incorporated by reference.

Examples of additional techniques which may be contemplated herein include those which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). Methods for producing chimeric antibodies are also known in the art and may be employed if desired. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety.

The present invention also contemplates a kit comprising one or more components, such as, but not limited to one or more primary antibodies that are capable of binding to any amino acid or polypeptide sequence described herein, one or more secondary antibodies that are capable of binding the primary antibody, one or more solutions or reagents for immunological analysis, for example, blocking or binding solution or the like, one or more polypeptides as described herein, said polypeptide optionally conjugated to a non-protein carrier, polypeptide carrier, heterologous amino acid sequence, support, dish, multi-well plate or the like, purification media for example, but not limited to remove abundant plasma proteins from samples that are collected, centrifugation media, immunoabsorption columns, resin, buffers, enzymes, one or more supports, dishes, multiwell plates, instructions for using any component or practicing any method as described herein, or any combination thereof.

EXAMPLES

Example 1: Sample Preparation Using Trypsin as a Protease

Frozen EDTA-plasma samples were thawed and immunodepleted using a MARS-14 (Agilent Technologies, USA) depletion column. The depleted plasma fraction was quantified for total protein by Bio-Rad DC Protein Assay. Twenty micrograms of total protein was reduced and then alkylated. The sample pH was adjusted to pH 8 with 1M $NH_4HCO_3$ and 1 microgram of trypsin enzyme was added to the sample and incubated for 16 hours at 37° C. The digested peptides were acidified with formic acid to a final concentration of 1% formic acid. A portion of each sample digest was pooled into one tube to be used for SRM method optimization. The remaining aliquots of the acidified digests were frozen at −80° C. until needed for SRM.

Example 2: Liquid Chromatography/Selected Reaction Monitoring-Mass Spectrometry (LC/SRM-MS)

An Eksigent nano-LC was used for chromatographic separation. The following gradient was used: 5% B-30% B in 60 minutes where solvent A is 98% water:2% acetonitrile and solvent B is 2% water:98% acetonitrile both with 0.1% formic acid. One microgram of tryptic peptides was loaded onto the column. The nano-LC was coupled to a 5500 Q TRAP® hybrid triple quadrupole/linear ion trap mass spectrometer (AB SCIEX, USA) through a nanoflow electrospray ionization source equipped with a 15 μm ID emitter tip. Tryptic peptides and SRM transitions were generated by MRMPilot 2.0 software (AB SCIEX, USA) based on common chemical rules of peptide fragmentation. The specificity of each peptide was verified using BLAST alignment against the NCBI-NR human protein database. The SRM method contained retention times to increase the number of transitions that can be monitored in one LC separation. Each patient sample was analyzed in triplicate using this SRM method.

Example 3: Preprocessing and Analysis of SRM-MS Dataset

The raw SRM-MS dataset was processed with Multi-Quant software version 1.1 to identify transition peaks and determine peak area. A 3 point Gaussian smoothing procedure was applied prior to peak area integration. Significance analysis was conducted using R software version 2.10.0. For each SRM transition (feature) measured in a given sample, within patient peak area mean and coefficient of variation (CV) over replicate experiments were calculated. For each feature, within-group mean peak area and CV were calculated for the MDD and control groups using within-patient mean peak area values from each group. Fold-change was derived for each feature from the ratio of mean peak area in MDD patient samples to mean peak area in control samples; positive fold-changes indicated increased expression in the MDD group. Peptides for which at least two transition features displayed a fold-change of 1.20 or greater and a within-group CV of 0.20 less (in both MDD and control groups) were retained.

Figure 1:
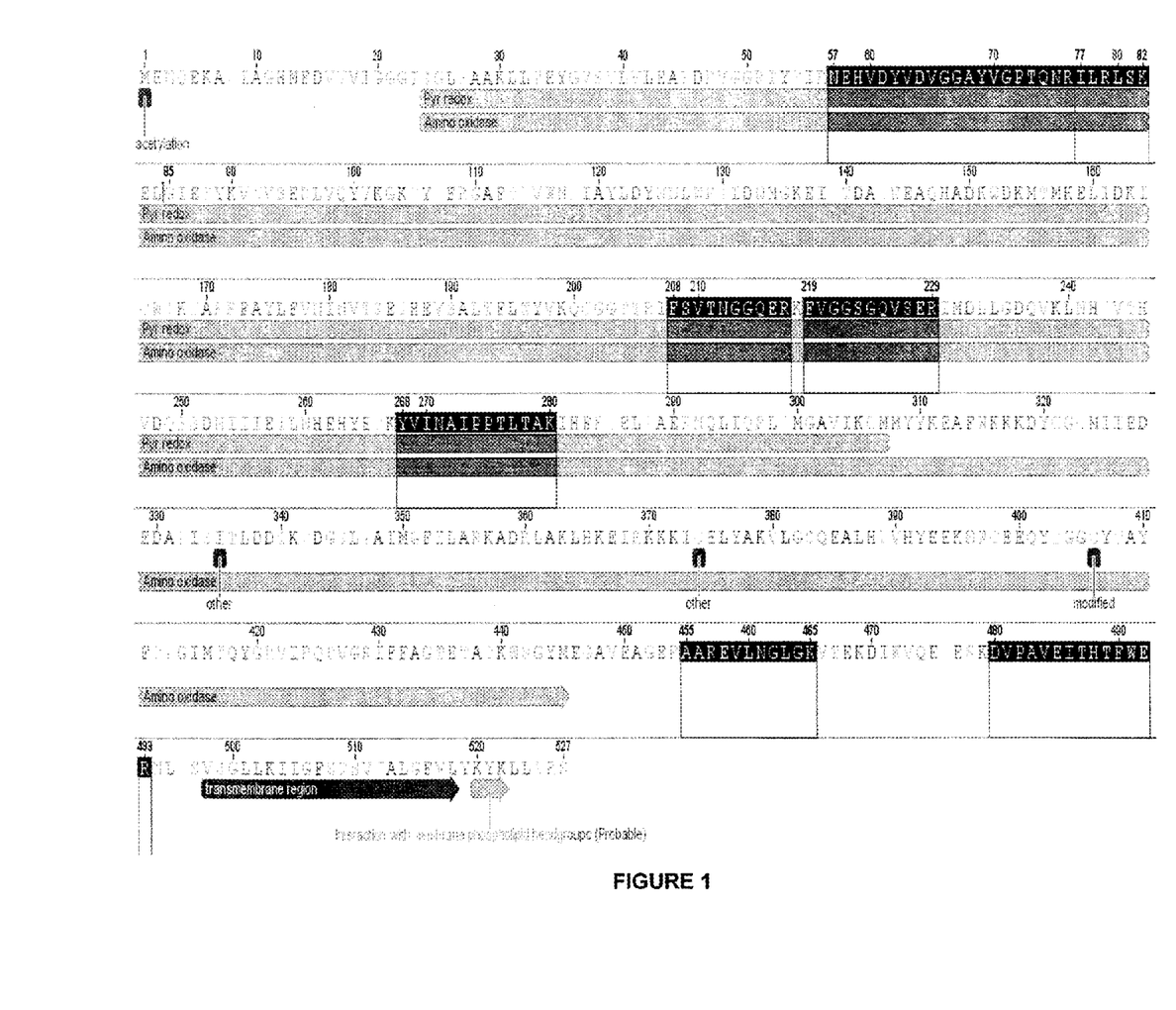
FIG. 1 is a schematic representation of a MAO-A protein sequence (SEQ ID NO: 8) with targeted transitions as marked.
Figure 2:
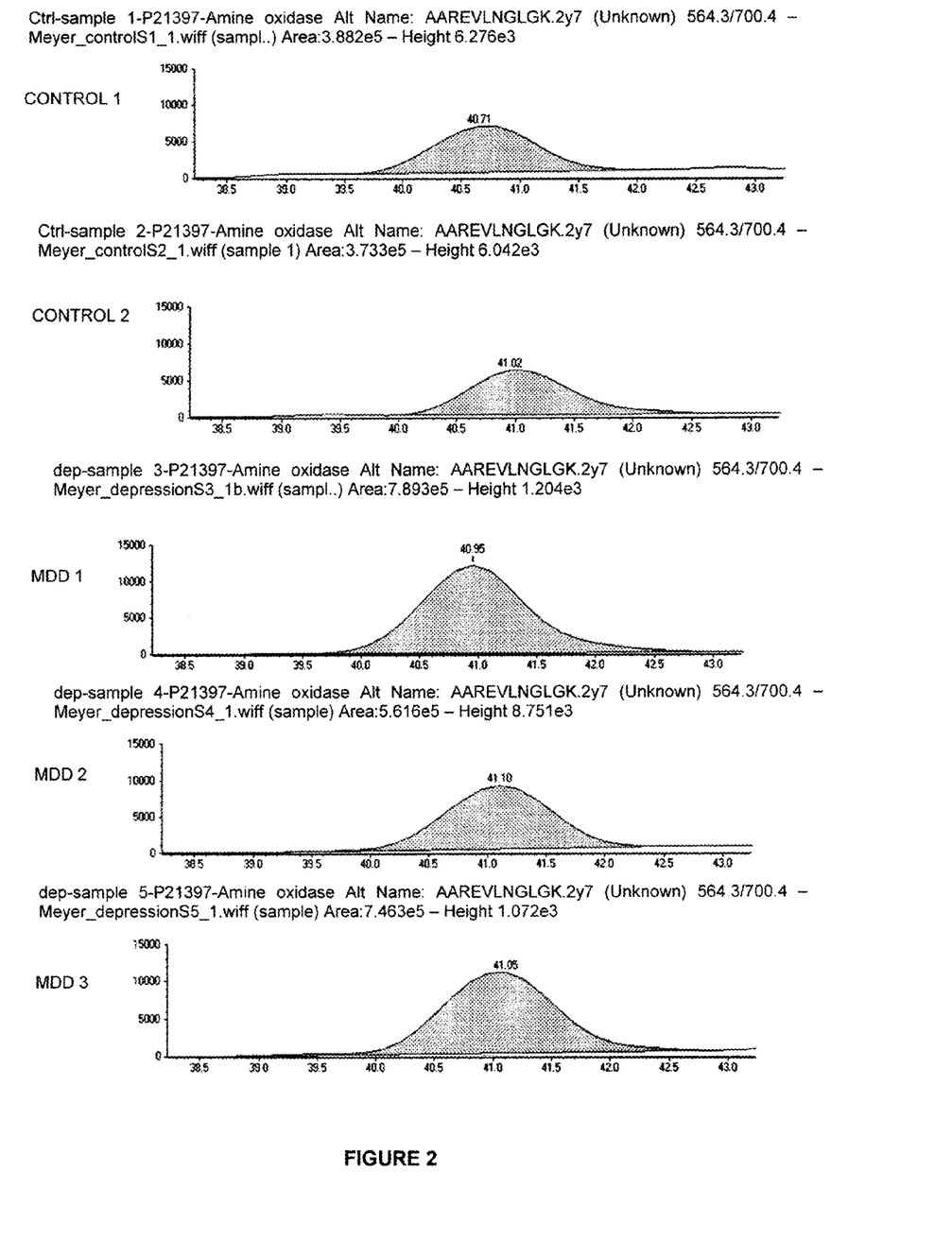
FIG. 2 is an extracted ion chromatogram for SRM-MS transitions for peptide AAREVLNGLGK (SEQ ID NO:5).
Figure 3:
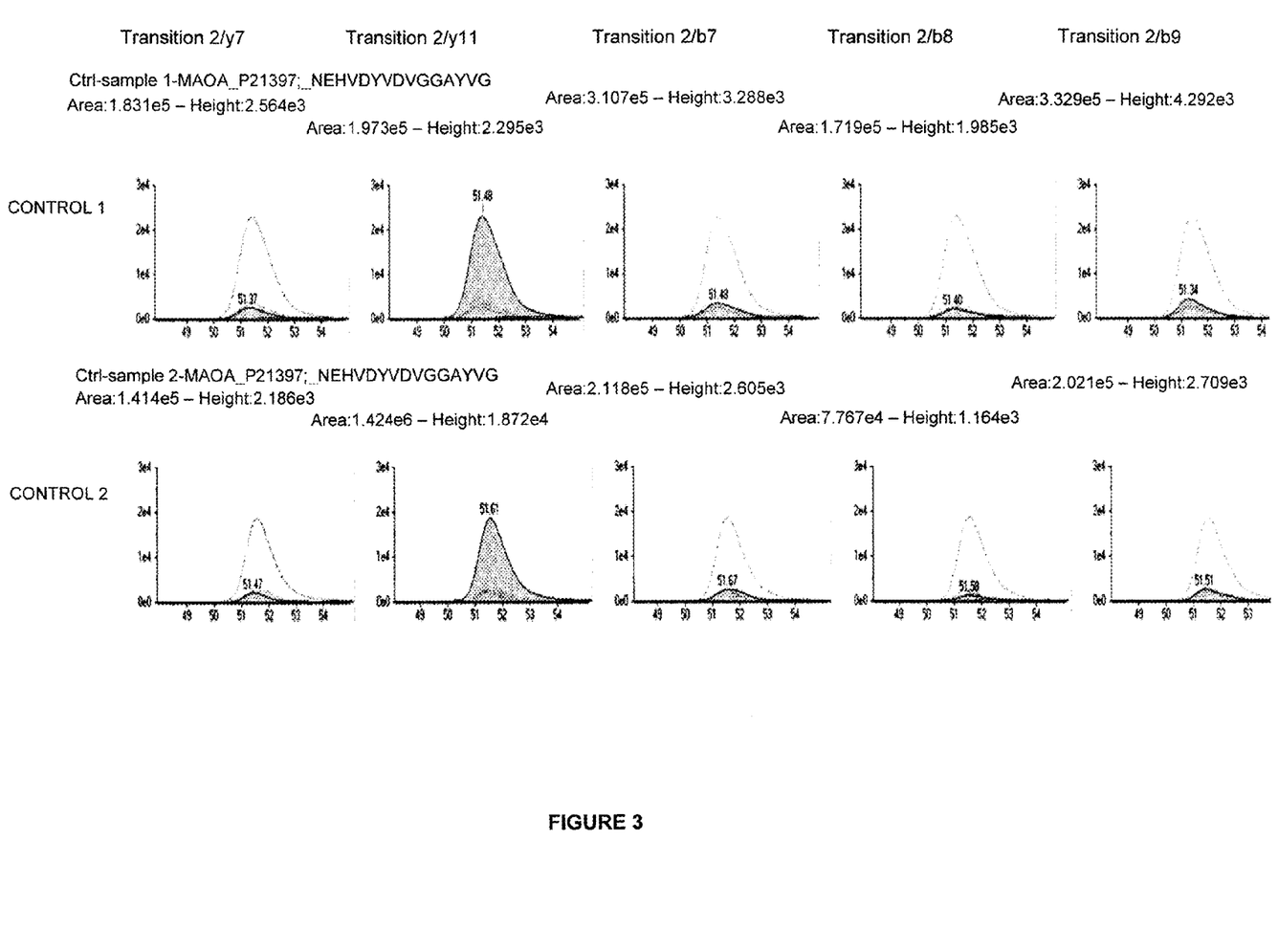
FIG. 3 is an extracted ion chromatogram for SRM-MS transition peaks for 5 transitions for peptide NEHVDYVD-VGGAYVGPTQNR (SEQ ID NO:1).
Figure 4:
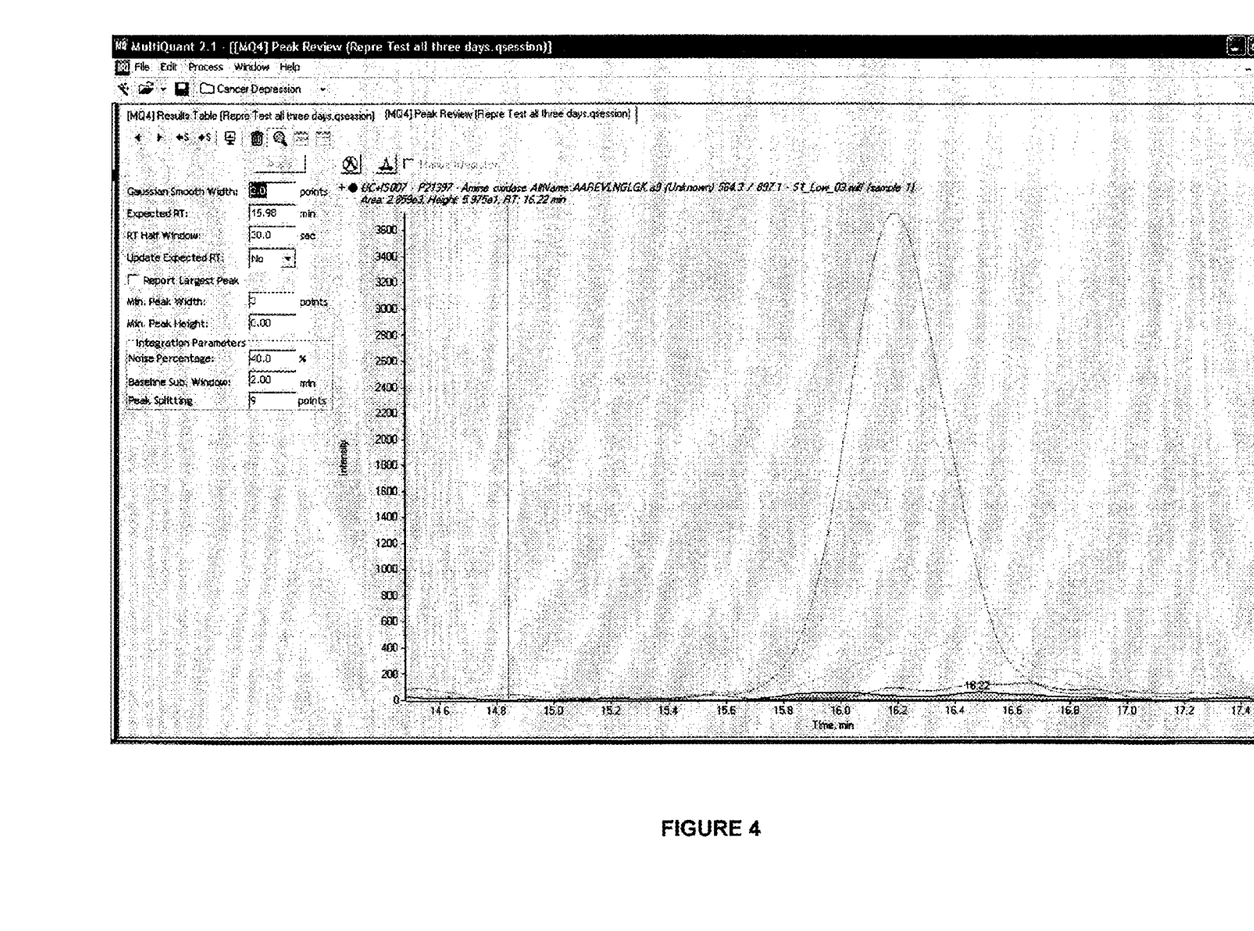
FIG. 4 is an extracted ion chromatogram for SRM-MS transition peaks for 5 transitions from peptide AAREV-LNGLGK (SEQ ID NO:5) derived from plasma specimens.
Figure 5:
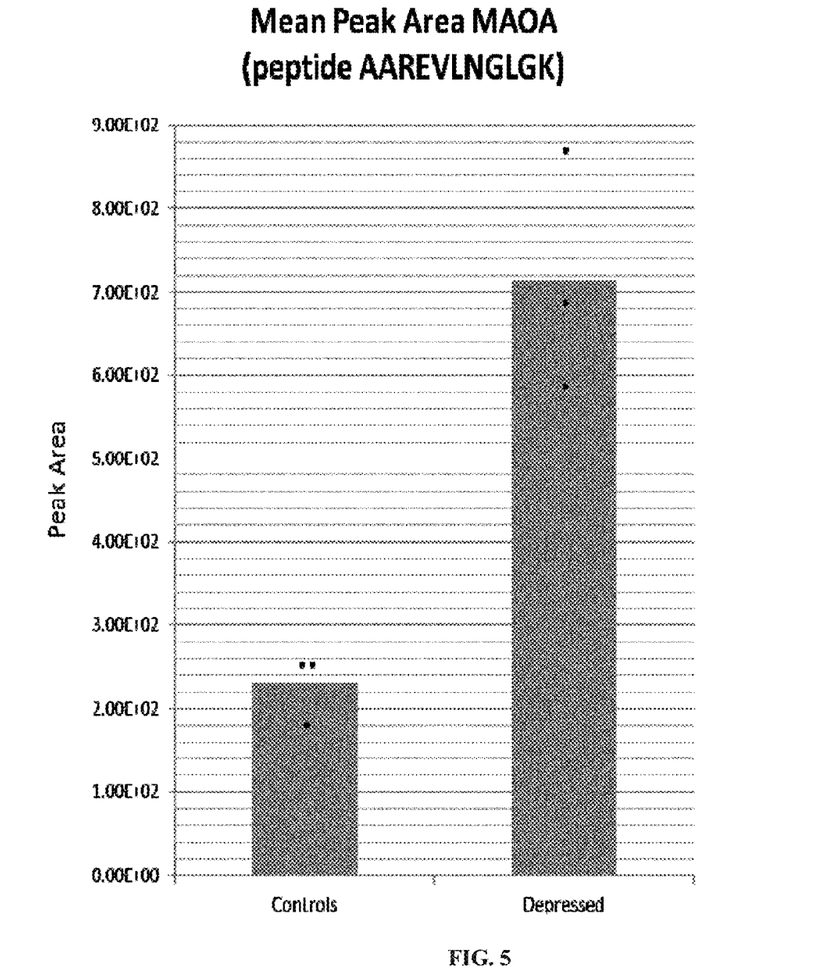
FIG. 5 shows mean peak area (counts) for analyte AAREVLNGLGK (SEQ ID NO:5) (Transition 564.3→811.3) from the plasma of depressed patients versus healthy controls, measured using SRM-MS methods. Dots represent scores for individual subjects.

These investigations identified transitions that produced a reliable and reproducible signal in human plasma. The targeted peptides are shown in FIG. 1. These peptides include:

(SEQ ID NO: 1)
NEHVDYVDVGGAYVGPTQNR;

(SEQ ID NO: 2)
ILRLSK;

(SEQ ID NO: 3)
FSVTNGGQER;

(SEQ ID NO: 4)
YVINAIPPTLTAK;

(SEQ ID NO: 5)
AAREVLNGLGK;
and (SEQ ID NO: 6)
DVPAVEITHTFWER.

Example 4: Peripheral MAO-A Levels Correspond to Levels Seen in Brain

Three MDD and two control plasma samples were analysed. These samples had previously undergone PET imaging and were shown to have relative changes similar to those seen in earlier studies. These specimens were then analysed in triplicate SRM-MS assays for multiple MAO-A transitions with the peptides: NEHVDYVDVGGAYVGPTQNR (SEQ ID NO:1); YVINAIPPTLTAK (SEQ ID NO:4); and AAREVLNGLGK (SEQ ID NO:5).

These peptides all show some overlap with MAO-B, but with sufficiently different sequences for the purposes of the present experiment (see Tables 1-3).

TABLE 1

NEHVDYVDVGGAYVGPTQNR (SEQ ID NO: 1)

| Align-ments | Accession | Entry name | Status | Protein names | Length | Identity | Score | E-Value | Gene names |
|---|---|---|---|---|---|---|---|---|---|
| | P21397 | AOFA_HUMAN | | Amine oxidase [flavin-containing] A | 527 | 100.0% | 152 | $6.0 \times 10^{-15}$ | MAOA |
| | P27338 | AOFB_HUMAN | | Amine oxidase [flavin-containing] B | 520 | 75.0% | 103 | $1.0 \times 10^{-7}$ | MAOB |

TABLE 2

AAREVLNGLGK (SEQ ID NO: 5)

| Align-ments | Accession | Entry name | Status | Protein names | Length | Identity | Score | E-Value | Gene names |
|---|---|---|---|---|---|---|---|---|---|
| | P21397 | AOFA_HUMAN | | Amine oxidase [flavin-containing] A | 527 | 100.0% | 76 | $5.0 \times 10^{-4}$ | MAOA |
| | P27338 | AOFB_HUMAN | | Amine oxidase [flavin-containing] B | 520 | 63.0% | 49 | 5.7 | MAOB |

TABLE 3

YVINAIPPTLTAK (SEQ ID NO: 4)

| Align-ments | Accession | Entry name | Status | Protein names | Length | Identity | Score | E-Value | Gene names |
|---|---|---|---|---|---|---|---|---|---|
| | P21397 | AOFA_HUMAN | | Amine oxidase [flavin-containing] A | 527 | 100.0% | 97 | $6.0 \times 10^{-7}$ | MAOA |
| | P27338 | AOFB_HUMAN | | Amine oxidase [flavin-containing] B | 520 | 90.0% | 69 | $8.0 \times 10^{-3}$ | MAOB |

A summary of the results from this experiment is given in Table 4 and sample peaks are given in the Figures. Results show generally consistent fold changes with what has been seen in the brain. Coefficients of variation were all below 20% and triplicate replications of SRM findings were also within acceptable limits of consistency.

TABLE 4

| Peptide | Transition (charge/ion) | Fold-Change | CV | Rep 1 Fold-Change | Rep 2 Fold-Change | Rep 3 Fold-Change |
|---|---|---|---|---|---|---|
| NEHVDYVDVGGAYVGPTQNR (SEQ ID NO: 1) | 2/y7 | 1.28 | 0.16 | 1.34 | 1.43 | 1.09 |
| | 2/y11 | 1.14 | 0.07 | 1.07 | 1.15 | 1.19 |
| | 2/b7 | 1.05 | 0.02 | 1.04 | 1.07 | 1.05 |
| | 2/b8 | 1.17 | 0.19 | 1.15 | 1.38 | 1.01 |
| | 2/b9 | 1.36 | 0.10 | 1.22 | 1.48 | 1.38 |
| AAREVLNGLGK (SEQ ID NO: 5) | 2/y7 | 1.69 | 0.05 | 1.57 | 1.71 | 1.78 |
| YVINAIPPTLTAK (SEQ ID NO: 4) | 2/y9 | 1.32 | 0.12 | 1.18 | 1.36 | 1.45 |

Example 5

Figure 6:
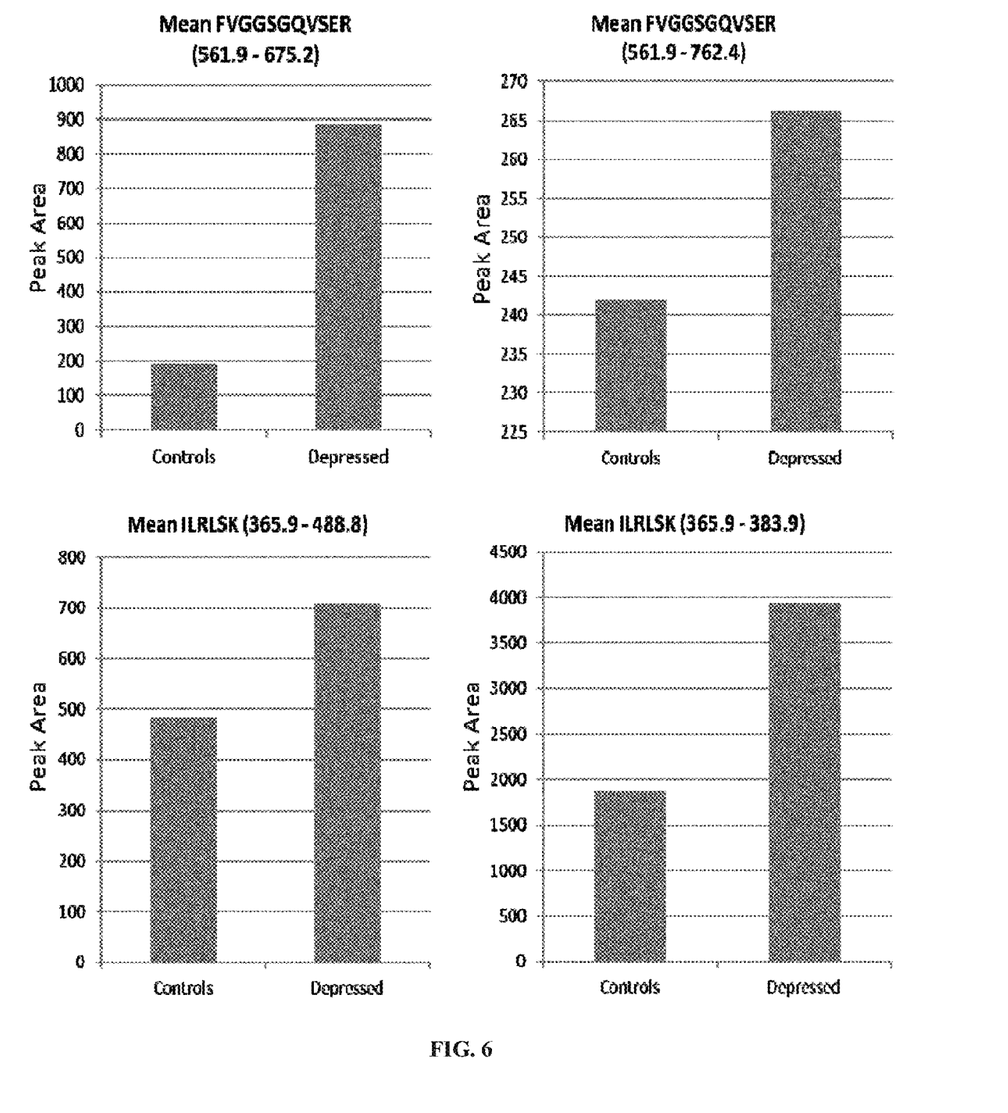
FIG. 6 shows peak areas for two transitions for each of the MAO-A peptides ILRLSK (SEQ ID NO:2) and FVGGS-GQVSER (SEQ ID NO:3), depressed vs controls.
Figure 7:
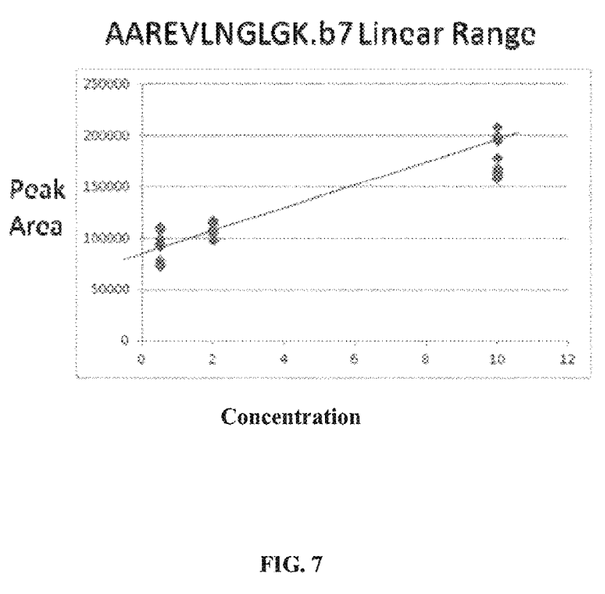
FIG. 7 shows the standard curve for AAREVLNGLGK (SEQ ID NO:5) as measured using SRM-MS and a labeled internal standard.

In a further study, PET scans revealed that the brains of 3 clinically depressed patients showed higher levels of MAO-A than seen in the brains of healthy controls. When plasma samples from these same individuals were depleted to remove the fourteen most abundant plasma proteins, digested with enzyme and analyzed using SRM-MS. We found more than threefold higher MAO-A levels in the depressed patients than in the healthy controls using the AAREVLNGLGK (SEQ ID NO: 5) transition (564.3→811.3, see FIG. 6). Other peptides also showed higher levels in depressed than controls, including ILRLSK (SEQ ID NO: 2) and FVGGSGQVSER (SEQ ID NO: 7) (FIG. 7) and the identity of all three peptides were confirmed using synthetic peptides of the same sequences. Without wishing to be bound by theory or limiting in any manner, the results presented herein suggest that the polypeptides can be employed as peripheral markers for an index of brain MAO-A concentration.

Example 6

In a further study, plasma MAO-A concentration (i.e. concentration of the AAREVLNGLGK (SEQ ID NO: 5)

fragment) was determined in a single subject who was asymptomatic for depression at the time of testing but had recovered from a past major depressive episode. The subject's relative plasma MAO-A concentration was determined to be approximately 8-fold greater than the mean plasma MAO-A concentration determined for healthy subjects and was interpreted to be an outlier. The subject went on to a recurrence of a major depressive episode within the following year as assessed in follow-up with the structured clinical interview for DSM-IV conducted by a trained rater (psychology PhD).

One or more currently preferred embodiments have been described by way of example. It will be apparent to persons skilled in the art that a number of variations and modifications can be made without departing from the scope of the invention as defined in the claims.

The invention claimed is:

1. A method for diagnosing major depressive disorder or susceptibility to major depressive disorder from a blood sample taken from a subject, said method comprising the steps of:
   a) subjecting the blood sample to protease-induced hydrolysis of monoamine oxidase-A (MAO-A) using trypsin, chymotrypsin, or a combination thereof, to generate polypeptides derived from MAO-A;
   b) detecting the polypeptides that are one or more markers of MAO-A in said blood sample;
   c) determining MAO-A concentration from said one or more markers; and
   d) comparing said MAO-A concentration in said blood sample to a control group which does not have major depressive disorder in order to diagnose major depressive disorder or susceptibility to major depressive disorder in the subject;
   wherein the one or more markers of MAO-A are one or more polypeptides comprising: AAREVLNGLGK (SEQ ID NO:5);
   wherein the one or more markers do not comprise full length MAO-A;
   and wherein:
   i) MAO-A concentration in the blood sample that is higher than the MAO-A concentration in the control group indicates a presence of major depressive disorder or susceptibility to major depressive disorder in the subject;
   ii) MAO-A concentration in the blood sample that is higher than the average MAO-A concentration in the control group indicates a presence of major depressive disorder or susceptibility to major depressive disorder in the subject; or
   iii) MAO-A concentration in the blood sample that is higher than a MAO-A concentration value previously determined for the control group indicates a presence of major depressive disorder or susceptibility to major depressive disorder in the subject.

2. The method of claim 1, wherein the protease is trypsin.

3. The method according to claim 1, wherein the subject is symptomatic for major depressive disorder and has previously been symptomatic for major depressive disorder.

4. The method according to claim 1, wherein the subject is asymptomatic for major depressive disorder and has not previously been symptomatic for major depressive disorder.

5. The method according to claim 1, wherein the subject is asymptomatic for major depressive disorder and has previously been symptomatic for major depressive disorder.

* * * * *